US006284537B1

(12) United States Patent
Offord Cavin et al.

(10) Patent No.: US 6,284,537 B1
(45) Date of Patent: Sep. 4, 2001

(54) IMMORTALIZED HUMAN CORNEAL EPITHELIAL CELL LINE

(75) Inventors: Elizabeth Offord Cavin, Poliez-Pittet; Andrea M. A. Pfeifer, St-Legier, both of (CH); Najam A. Sharif, Arlington, TX (US); Yvonne Tromvoukis, Mollie-Margot (CH)

(73) Assignee: Nestec S.A., Vevey (CH)

( * ) Notice: Subject to any disclaimer, the term of this patent is extended or adjusted under 35 U.S.C. 154(b) by 0 days.

(21) Appl. No.: 08/997,588

(22) Filed: Dec. 23, 1997

(30) Foreign Application Priority Data

Dec. 24, 1996 (EP) .................................................. 96203707

(51) Int. Cl.⁷ ............................. C12N 5/08; C12N 5/10
(52) U.S. Cl. .................. 435/366; 435/320.1; 424/130.1
(58) Field of Search ................................. 435/240.2, 366, 435/320.1, 371; 424/130.1

(56) References Cited

U.S. PATENT DOCUMENTS

| 5,585,265 | 12/1996 | Kahn et al. | 435/240.2 |
| 5,672,498 | * 9/1997 | Walker et al. | 435/240.2 |

FOREIGN PATENT DOCUMENTS

| 0 802 257 | 10/1997 | (EP) . |
| WO 94/05472 | 3/1994 | (WO) . |
| WO 96/07750 | 3/1996 | (WO) . |

OTHER PUBLICATIONS

GeneBank databank (Accession No. M64753).
Albers et al., 1991, "In vivo intestinal metabolism of 7–ethoxycoumarin in the rat: Production and distribution of phase I and II metabolites in the isolated, perfused intestinal loop", *Toxicol. & Applied Pharmacol.* 109:507–513.
Araki et al., 1993, "Immortalization of rabbit corneal epithelial cells by a recombinant SV40–adenovirus vector", *Invest Ophthalmol. Visual Sci.* 34:2665–2671.
Araki–Sasaki et al., 1995, "An SV40–immortalized human corneal epithelial cell line and its characterization", *Invest Ophth. & Visual Sci.* 36:614–621.
Bazan et al., 1991, "Platelet–activating factor (PAF) accumulation correlates with injury in the cornea", *Exp. Eye Res.* 52:481–491.
Bazan et al., 1993, "Platelet–activating factor induces collagenase expression in corneal epithelial cells", *Proc. Natl. Acad. Sci. USA* 90:8678–8682.
Chen et al., 1987, "High–efficiency transformation of mammalian cells by plasmid DNA", *Mol. & Cell. Biol.* 7:2745–2752.
Conners et al., 1995, "A closed eye contact lens model of corneal inflammation", *Inves. Ophth. & Visu Sci.* 36:828–840.

Cubitt et al., 1993, "IL–8 gene expression in cultures of human corneal epithelial cells and keratocytes", *Invest Ophth. & Visual Sci.* 34:3199–3206.
Cubitt et al. 1995, "Differences in Interleukin–6 gene expression between cultured human corneal epithelial cells and keratocytes", *Invest. Ophth. & Visual Sci.* 36:330–336.
Dutt et al., 1994, "Establishment of Human T Antigen Gene with potential to Undergo Neuronal Differentiation", *DNA and Cell Biology* 13:909–921.
Ellis et al., 1995, "Substrate specificity of an aflatoxin–metabolizing aldehyde reductase", *Biochem. J.* 312:535–541.
Gibson et al., 1994, "Serum free medium increases expression of markers of differentiation in human colonic crypt cells", *Gut* 35:791–797.
Gumbiner, 1992, "Epithelial morphogenesis", *Cell* 69:385–387.
Hainsworth, 1991, "Modified culture method for human corneal epithelial cells", *J. Tiss Cult. Meth.* 13:45–48.
Jat et al., 1989, "Cell lines established by a temperature–sensitive simian virus 40 large–T–antigen gene are growth restricted at the nonpermissive temperature", *Mol. Cell. Biol.* 9:1672–1681.
Kahn et al., 1993, "Human corneal epithelial primary cultures and cell lines with extended life span: In vitro model for ocular studies", *Invest. Ophth. & Visual Sci.* 34:3429–3441.
Kennedy et al., 1995, "Novel production of Interleukin–1 receptor antagonist peptides in normal human cornea", *J. Clinical Invest.* 95:82–88.

(List continued on next page.)

Primary Examiner—Scott W. Houtteman
(74) Attorney, Agent, or Firm—Pennie & Edmonds LLP

(57) ABSTRACT

Immortalized human cornea). epithelial cell line capable of becoming stratified, and capable of expressing (1) metabolic markers specific for non-immortalized human epithelial cells such as vimentin, cytokeratins, connections between the cells, cytochrome P450s, a glutathione-S-transferase, Cu/Zn-superoxide dismutase, glutathione peroxidase, aldehyde reductase and catalase; (2) metabolic differentiation markers specific for non-immortalized human cornea). epithelial cells such as the cytokeratin of 64 kfl, the glutathione-stransferase hGST 5.8, and the profile of cytokines and growth factors comprising the compounds TNFα, IL-1β, IL-1α, IL-6, IL-8, GM CSF-β, IL-ra, TGF-β1, TGF-β2, TGFα, EGF, PDGF-β; (3) and markers specific for an inflammatory reaction such as collagenase I, the bradykinin, histamine and PAF receptors, and the system for transduction of an inflammatory signal by the phosphoinositides. Process for identifying the mutagenic, toxic or beneficial effect of an agent on the metabolism of the corneal cells, in which (1) an agent suspected of being a mutagenic, toxic or beneficial agent for the metabolism of the cells of the human cornea is reacted, cultured or brought into contact with a culture comprising a cell line according to the invention, and (2) the effects of the said agent on the said cell line are determined or measured.

5 Claims, 4 Drawing Sheets

OTHER PUBLICATIONS

Kernacki et al., 1994, "Characterization of the inflammatory response induced by corneal infection with *Pseudomonas aeruginosa*", *J. Ocul. Pharmacol.* 10:281–288.

Kiritoshi et al., 1991, "Differentiation in the cultured limbal epithelium as defined by keratin expression", *Invest. Ophth. & Visual. Sci.* 32:3073–3077.

Kulkarni et al., 1995, "Characterization of human buccal epithelial cells transfected with the simian virus 40 T–antigen gene", *Carcinogenesis* 16:2515–2521.

Li et al., 1995, "Three patterns of cytokine expression potentially involved in epithelial–fibroblast interactions of human ocular surface", *J. Cellular Physiol.* 163:61–79.

Lynch et al., 1991, "Production of high–titer helper virus––free retroviral vectors by cocultivation of packaging cells with different host ranges", *J. Virol.* 65:3887–3890.

Mann et al., 1983, "Construction of a retrovirus packaging mutant and its use to produce helper–free defective retrovirus", *Cell* 33:153–159.

McKinnon et al., 1995, "Characterisation of CYP3A gene subfamily expression in human gasstrointestinal tissues", *Gut* 36: 259–267.

Mercurio et al., 1995, "Expression of cytochrome P450 mRNAs in the colon and the rectum in normal human subjects", *Biochem. Biophy. Res. Comm.* 210:350–355.

Moll et al., 1982, "The catalog of human cytokeratins: Patterns of expression in normal epithelia tumors and cultured cells", *Cell* 31:11–24.

Pfeifer et al., 1993, "Simian virus 40 large tumor antigen––immortalized normal human liver epithelial cells express hepatocyte characteristics and metabolize chemical carcinogens", *Proc. Natl. Acad. Sci. USA* 90:5123–5127.

Reiners et al., 1990, "Modulation of catalase activities in murine epidermal cells as a function of differentiation and exposure to 12–O–tetradecanoylphorbol–13–acetate", *Carcinogenesis* 11:957–963.

Richard et al., 1990, "Vimentin expression in normal human keratinocytes grown in serum–free defined MCDB 153 medium", *Arch. Dematol. Res.* 282:512–515.

Rosenbaum et al., 1995, "Detection of mRNA for the cytokines, Interleukin–1α and Interleukin–8, in corneas from patients with pseudophakic bullous keratopathy", *Invest. Opht. & Visual Sci.* 36:2151–2155.

Sharif et al., 1991, "Identification of $B_2$–bradykinin receptors in guinea pig brain regions, spinal cord and peripheral tissues", *Neurochem. Int.* 18:89–96.

Sherif et al., 1993, "The neuropeptide bradykinin stimulates phophoinositide turnover in HSDM1C1 cells: $B_2$–antagonist–sensitive responses and receptor binding studies", *Neurochem. Res.* 18:1313–1320.

Sharif et al., 1994, "Emedastine: A potent, high affinity histamine $H_1$–receptor–selective antagonist for ocular use: Receptor binding and second messenger studies", *J. Ocular Pharmacol.* 10:653–664.

Singh et al., 1985, "Characterization of glutathione S–transferases of human cornea", *Exp. Eye Res.* 40:431–437.

Singhal et al., 1995, "Novel human ocular glutathione S–transferases with high activity toward 4–hydroxynonenal", *Invest. Ophth. & Visual Sci.* 36:142–150.

Stockschlaeder et al., 1991, "L–histidinol provides effective selection of retrovirus–vector–transduced keratinocytes without impairing their proliferative potential", *Human Gene Therapy*, 2:33–39.

Wilson et al., 1992, "EGF, EGF receptor, basic FGF, TGF beta–1, and IL–1 alpha mRNA in human corneal epithelial cells and stromal fibroblasts", *Invest. Opth. & Visual Sci.* 33:1756–1762.

Wilson et al., 1995, "Optimization of calcium phosphate transfection for bovine chromaffin cells: Relationship to calcium phosphate precipitate formation", *Ana Biochem.* 226:212–220.

Derwent WPI Acc. No: 97–505472/199747, English language abstract of EP 802257.

* cited by examiner

- CNCM I-1777 EC50 = 3.26 × 10⁻⁹ M
- PRIMARY EC50 = 2.02 × 10⁻⁹ M

IMMORTALIZED HUMAN CORNEAL EPITHELIAL CELL LINE

FIELD OF THE INVENTION

The subject of the present invention is new immortalized human corneal epithelial cell lines as well as their use in processes for the identification of agents which are mutagenic, toxic or beneficial to the metabolism of the corneal cells.

BACKGROUND ART

For many years, efforts have been made to develop human cell lines adapted to the study of human diseases such as infections, inflammations or cancers, for example. Among the cells often involved in the onset of diseases, there are the epithelial cells which are sensitive to the surroundings of the human body.

The epithelial cells differ from other cells of the human body in the expression of compounds or structures which are found only in the epithelial cells, such as, for example, cytokeratins (Moll et al., Cell, 31, 11–24, 1982), connections between the cells (Gumbiner et al., Cell, 69, 385–387, 1992), and vimentin (Richard et al., Arch. Dematol. Res., 282, 512–515, 1990).

Other compounds are also generally found in human epithelial cells, but not only in the epithelial cells, such as the cytochrome P4505 (Mercurio et al., Biochem. Biophys. Research Communications, 210, No.2, 350–355, 1995; McKinnon et al., Gut, 36, 259–267, 1995), the enzymes involved in the defence against cellular oxidation (Cu/Zn-superoxide dismutase, glutathione peroxidase, glutathione reductase and catalase: Albers et al., Toxicology and Applied Pharmacology, 109, 507–513, 1991) and/or in the detoxification of electrophiles ($\alpha$-, $\mu$- or $\pi$-glutathione-S-transferases: Singh et al. Exp. Eye Res., 40, 431–437, 1985; aldehyde reductase: Ellis et al., Biochemical J., 312, 535–541, 1995). The epithelial cells of the human cornea also differ from other human epithelial cells in the expression of compounds which are found only in the epithelial cells of the cornea, such as for example the cytokeratin of 64 kD and the glutathione-S-transferase hGST 5.8 which are found in the ocular tissues (hGST 5.8: Singhal et al., Invest. Ophthalmol. Vis. Sci., 36, 142–150, 1995; 64 kD: Kiritoshi et al., Invest. Ophthalmol. Vis. Sci., 32, 3073–3077, 1991).

Analysis of the expression of certain cytokines and growth factors in the epithelial cells of human cornea, without inflanimatory stimulation, has already been determined by Cubitt et al. (1993, Invest. Ophthanol. & Vis. Sci. 34:3199–3206; and 1995, Invest. Ophthamol. & Vis. Sci. 36:330–336), Wilson et al. (1992, Invest. Ophthamol. & Vis. Sci. 33:1756–1762), Kennedy et al. (1995, J. Clinical Invest. 95:82–88), and DeQuan et al. (1995, J. Cellular Physiol. 163:61–79). Moreover, Rosenbaum et al. have suggested that the cytokine profile of the corneal cells could be a means for effectively detecting the presence of certain diseases of the cornea (Invest. Ophthalmol. Vis. Sci., 36, 2151–2155, 1995). The profile of expression of certain cytokines and growth factors in the epithelial cells of the cornea therefore makes it possible to characterize and differentiate the normal corneal epithelial cells from the other cells, and in particular from the abnormal corneal epithelial cells.

Moreover, the methods of screening for molecules which are noninflammatory for the eyes involve laboratory animals. To overcome the fact that there are substantial morphological and biochemical differences between the human eyes and those of these animals, Hainsworth et al. propose to carry out these screening tests on primary epithelial cell cultures of cornea (J. Tissue Culture Meth., 13, 45–48, 1991). Unfortunately, primary cell cultures of cornea stop multiplying after one or two passages, each passage consisting of subculturing the cells in fresh medium after growing until they become confluent. Furthermore, these primary cells do not survive freezing in liquid nitrogen.

To overcome these disadvantages, human corneal epithelial cell lines have been developed by Kahn et al. (Invest. Opthalmol. Vis Sci., 34, 3429–3441, 1993) and Araki-Sasaki et al. (Invest. Opthalmol. Vis. Sci., 36, 614–621, 1995). Unfortunately, these lines are not yet fully satisfactory.

Indeed, the lines developed by Kahn et al. are not completely immortalized because they retain certain original differentiation characteristics up to about 25 successive culture passages (see Kahn et al.). These lines also release SV40 viruses into the culture medium (see the Araki-Sasaki et al. analysis). Finally, it is not known if they effectively express other differentiation markers, such as glutathione-S-transferase hGST 5.8, and an appropriate cytokine and growth factor profile, as well as markers which are specific or necessary for an inflammatory reaction.

The immortalized lines developed by Araki-Sasaki et al. are, on the other hand, incapable of becoming stratified in comeal reconstruction trials in vivo (see Araki-Sasaki et al.), and it is not known if they express certain differentiation markers, such as glutathione-S-transferase hGST 5.8, and an appropriate cytokine and growth factor profile, as well as markers which are specific or necessary for an inflammatory reaction.

The aim of the invention is to provide new human comeal epithelial cell lines which are genetically and physiologically similar to the normal epithelial cells of the human cornea, to the extent that they can be used effectively in trials for screening potentially inflammatory molecules.

SUMMARY OF THE INVENTION

To this end, the invention relates to any immortalized human comeal epithelial cell lines capable of becoming stratified, and capable of expressing metabolic differentiation markers specific for non-immortalized human epithelial cells, metabolic markers specific for non-immortalized human corneal epithelial cells, and markers specific for an inflammatory reaction.

Another aspect of the invention relates to a new process for identifying the mutagenic, toxic or beneficial effect of an agent on the metabolism of the cells of the cornea, in which (1) a culture comprising a cell line according to the invention is reacted with an agent suspected of being a mutagenic, toxic or beneficial agent for the metabolism of the cells of the human cornea, and (2) the effects of the said agent on the said cell line are determined.

The invention also relates to a diagnostic kit comprising the immortalized human corneal epithelial cells according to the invention and reagents for determining a metabolic response of the said cells to mutagenic, toxic or beneficial agents for the said cells.

Finally, the subject of the invention is also any uses of the cell lines according to the invention, in processes for the identification of mutagenic, toxic or beneficial agents for the metabolism of the corneal cells, as well as any uses of these lines as active pharmaceutical agent.

DETAILED DESCRIPTION OF THE INVENTION

Figure 1:
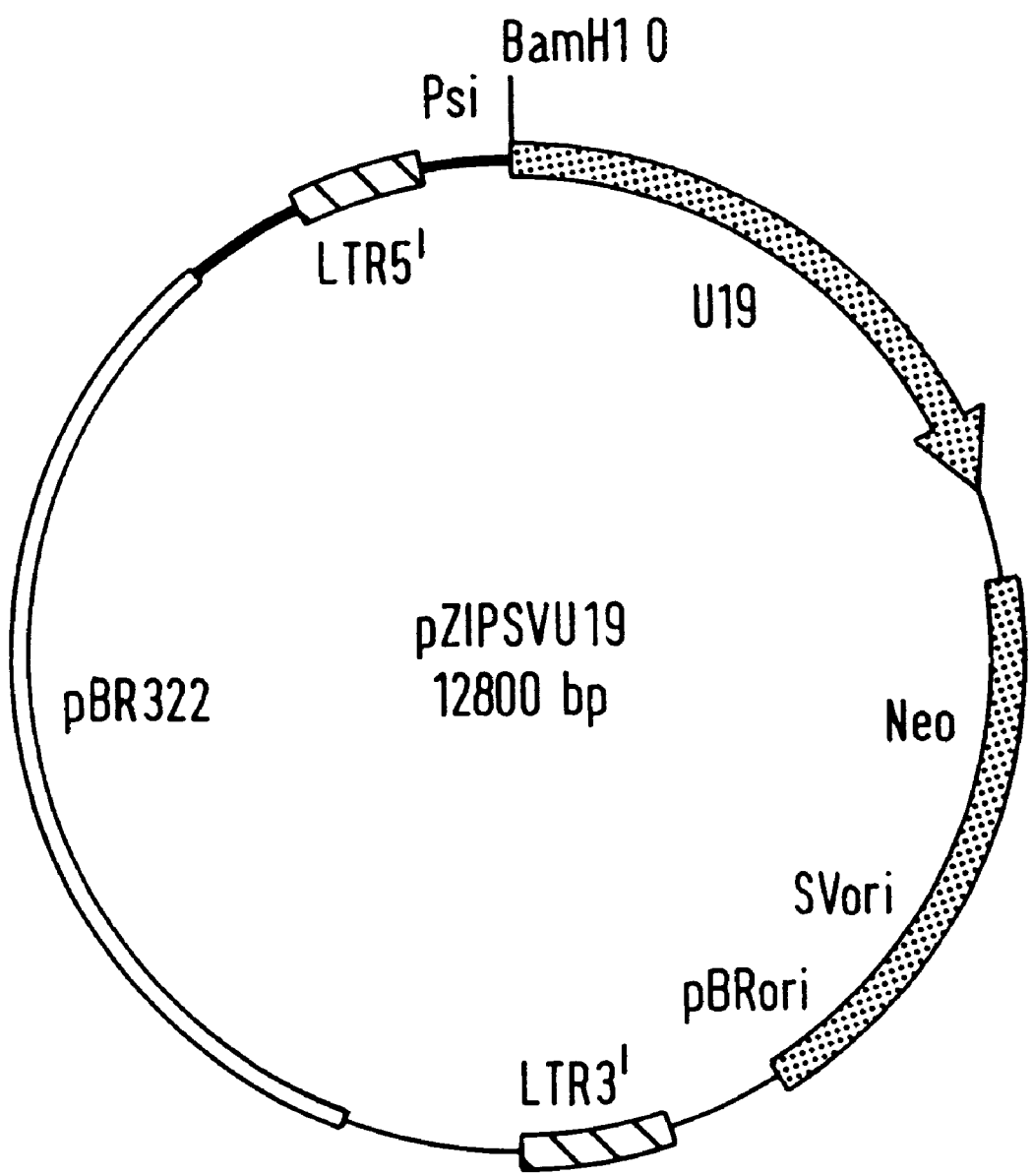
FIG. 1: schematic representation of the plasmid pZIPSVU19 which was used to prepare the vector pl/SV40U19 intended to immortalize the primary epithelial cells of the human cornea.

Within the framework of the present invention, the expressions "normal cells', "primary cells" and non-immortalized cells" designate epithelial cells of the human cornea which can be collected from the cornea of a healthy adult not having crippling physiological or genetic deficiencies, and which can be cultured for a limited time without losing their original differentiation characteristics.

On the other hand, the expression "immortalized cells" designates cells which have undergone a genetic manipulation, by means of a DNA construct, which makes them capable of multiplying indefinitely, that is to say, at more than 25 passages, preferably at least 60 passages.

Likewise, the word "passage" designates the process consisting of taking an aliquot of a confluent or saturation culture of a cell line, in inoculating a fresh medium, and in culturing the line until confluence or saturation is obtained. The cell lines are thus traditionally cultured by successive passages in fresh media. It should be noted that the cell lines may lose their original differentiation characteristics after several successive passages. It is therefore extremely advantageous to be able to have a line whose characteristics are conserved even after numerous passages, preferably at least 30 to 60 passages.

Finally, the expression "original differentiation characteristics" designates both the markers found specifically on the human epithelial cells and the differentiation markers found specifically on the epithelial cells of the human cornea.

Preferably, the immortalized human corneal epithelial cell lines according to the invention do not express tumour markers, that is to say, do not have carcinogenic genes or do not express messenger RNAs (mRNAs), proteins or differentiated cellular structure and characteristic of the transformation of the cells into tumour cells. The presence of these markers may be detected by hybridization or PCR of their DNA with a specific probe, by means of antibodies, and/or by electron microscopy, for example. The presence of a marker in a cell does not mean that the said cell is capable of conferring a cancer, after a few months, on a mouse without immune defence, but rather reflects a cancerous transformed state of the cells compared with the original cells from which they are derived.

Preferably, the lines according to the invention also lack viruses, that is to say, are incapable of producing the viruses which initially immortalized them, in contrast to the lines developed by Kahn et al. (see the introduction of Araki-Sasaki et al.).

The lines according to the invention should be capable of becoming stratified, that is to say, capable of becoming organized into successive strata For that, the lines according to the invention simply have to be cultured until they are confluent in a serum-free medium comprising 1.5 mM $CaCl_2$, and then it must simply be visually observed if the cells develop into strata, for example.

The lines according to the invention express, on the other hand, metabolic markers specific for normal human epithelial cells, that is to say, markers generally found in the epithelial cells.

These specific markers may be a messenger RNA (mRNA), a protein and/or a differentiated cellular structure capable of being derived from epithelial cells of the skin, the eye, the intestinal tract or the liver, for example. Preferably, the human epithelial cells according to the invention express at least two markers chosen from the group formed by vimentin, cytokeratins, connections between the cells (also called "tight junctions"), cytochrome P450s, glutathione-S-transferase (GST), Cu/Zn-superoxide dismutase (SOD), glutathione peroxidase (GP), glutathione reductase (GR), catalase (CA) and aldehyde reductase (AR).

It may also be noted that the lines according to the invention may express enzymes involved in cellular oxidation (SOD, GP, GR and CA) and/or the detoxification of electrophiles (GST, AR). These lines are thus particularly adapted to the study of the phenomena of inflammations or irritations of the human cornea.

The cell lines according to the invention also express metabolic differentiation markers which are specific for the corneal cells, especially the epithelial cells of the human cornea (see Reiners et al., Carcinogenesis, 11, 957–963, 1990). These differentiation markers may be an mRNA, a protein or a differentiated cellular structure. Preferably, the lines according to the invention express at least 2 differentiation markers chosen from the group formed by the cytokeratin of 64 kD, glutathione-S-transferase hGST 5.8, and a cytokine and growth factor profile comprising the compounds TNFα, IL1β, IL-1α, IL-6, IL-8, GM CSF-β, IL-ra, TGF-β1, TGF-β2, TGFα, EGF, PDGF-β.

The lines according to the invention are also capable of expressing at least one marker specific for an inflammatory reaction, that is to say, a molecule which is detectable when the cell reacts to an inflammatory stimulus and/or a molecule or a structure which is necessary for an inflammatory reaction.

The inflammatory stimuli may be induced when the lines according to the invention are brought into contact with a microorganism of the *Pseudomonas aeruginosa* species (Kemacki et al., J. Ocul. Pharmacol., 10, 281–288, 1994), with the platelet activating factor PAF (Bazan et al., Exp. Eye Research, 52:481–491, 1991), with 12-O-tetradecanoylphorbol (TPA: tumour promoting agent), with histamine (Sharif et al., J. Ocul. Pharmacol., 10, 653–664, 1994), with bradykinin (Sharif et al., Neurochem. Int. 18, 89–96, 1991), or with other inflammatory compounds, for example.

Collagenase I is a marker which is easily detectable when a line is subjected to an inflammatory stimulus (Bazan et al., Proc. Natl. Acad. Sci. USA, 90, 8678–S682, 1993). Other markers may also be detected, such as c-fos (see Bazan et al.), the arachidonic intermediates 12-HETE and 12-HETrE (Conners et al., Invest. Opthalmol. Vis. Sci., 36, 828–840, 1995) or a new cytokine and growth factor profile, for example.

The lines according to the invention are also capable of expressing at least one marker necessary for an inflammatory reaction, such as for example the bradykinin receptor, the histamine receptor, the PAF receptor, and the system for transduction of a signal by the phosphoinositides (phosphoinositide turnover signal transduction pathway; Sharif et al., Neurochem. Res., 12, 1313–1320, 1993).

The invention also relates, in particular, to an immortalized line according to the invention which was deposited, under the Budapest Treaty, with the Collection Nationale de Cultures de Microorganismes, Institut Pasteur, 25 rue du Docteur Roux, 75724 Paris, on Oct. 22, 1996, where it received the deposit number CNCM I-1777.

The epithelial lines according to the invention advantageously conserve their original differentiation characteristics even after numerous passages, especially at least 25 passages, preferably at least 30 to 100 passages.

To obtain the lines according to the invention, it is possible to prepare a culture of primary epithelial cells derived from the human cornea, to infect the culture with a recombinant virus and to culture the immortalized cells in a serum-free culture medium. To this end, persons skilled in the art have available numerous serum-free culture media. As a guide, there may be mentioned the serum-free media described by Gibson et al., (Gut, 35 791–797, 1991), Pfeifer et al. (Proc. Natl. Acad. Sci. USA, 90, 5123–5127, 1993), Kulkani et al. (Carcinogenesis, 16, No. 10, 2515–2521, 1995), or in European patent application No. EP96201064.1 and U.S. application Ser. No. 08/576,483, for example. A serum-free medium which is perfectly adapted to the need of this process is the KGM medium (Clonetics, US).

Preferably, the following steps are used:

(1) a sample of epithelial tissues of a human cornea is obtained;

(2) this sample is prepared for the purpose of its culture in vitro;

(3) the epithelial cells are inoculated into a serum-free culture medium and on culture plates comprising a coating which facilitates the attachment of the cells and their growth;

(4) the medium is changed as many times as necessary in order to optimize the confluent growth;

(5) the cells are infected with a recombinant virus;

(6) and the immortalized cells are cultured in a serum-free culture medium.

In greater detail, stage 1) relates to the obtaining of samples of corneal cells from normal individuals during surgical acts. In stage 2), the sample may be washed in the culture medium, cut into pieces, and the epithelial part separated from other tissues by physical and/or chemical means. For example, the pieces of tissue may be placed in a solution comprising a protease for a time sufficient to achieve separation of the cells.

In stage 3), the epithelial cells may be inoculated into a serum-free culture medium, the culture plates having a coating consisting of a 0.01–1% gelatin solution, for example.

In stage 4), the culture medium containing the epithelial cells is changed as many times as necessary so as to optimize a confluent growth. Preferably, the medium is replaced every two days. After having reached a confluence of the order of 90% of the available surface area, which generally occurs 10 to 14 days after the inoculation, the cells are separated by treatments in a solution of proteases.

The separated cells are transferred in stage 5) into a fresh culture medium and then the cells are then conventionally infected with a recombinant virus. Numerous transfection techniques are available to persons skilled in the art. By way of example, there may be mentioned the techniques described in PCT International Publication WO 96/07750, by Claudia Chen et al. (Mol. and Cell. Biol., 7, 2745–2752, 1987) or by Wilson et al. (Analytical Biochemistry, 226, 212–220, 1995).

Preferably, a recombinant SV40 virus comprising the T Antigen (T-Ag), an inactivated virus replication origin and a selectable gene are used. By way of example, there may be used the DNA construct pLXSHD+SV40+ described by Stockshlaeder et al. whose sequence is available in the GenBank databank (accession No. M64753; Human Gen. Therapy, 2, 33–39, 1991).

Other appropriate vectors may be just as easily constructed by persons skilled in the art from commercially available vectors comprising the gene encoding T-Ag, a selectable gene and/or an inactivated virus replication origin. By way of example, there may be prepared the construct pI/SV40U19 by creating BamHI sites at the ends of the BglI-HpaI fragment of SV40, and by cloning this fragment into the BamHI site of the plasmid pZIPSVU19 described in FIG. 1 below, and by Jat et al., Mol. Cell. Biol., 9, 1672–1681, 1989.

In stage 6), the epithelial cells are transferred into a fresh growth medium, on culture plates having the coating described above.

Knowing the new and original properties of the epithelial cell lines according to the invention, their application may be envisaged in immunological, pharmacological and toxicological studies.

The lines according to the invention are thus particularly adapted for screening mutagenic, toxic or beneficial agents for the metabolism of the cells of the cornea, for example in a process in which (1) an agent suspected of being a mutagenic, toxic or beneficial agent for the metabolism of the cells of the cornea is reacted, cultured or brought into contact with a culture comprising a cell line according to the invention, and (2) the effects of the said agent on the said cell line are determined or measured.

It may therefore also be envisaged to prepare a diagnostic kit comprising the epithelial cells according to the invention and reagents for determining a metabolic response of the said cells to mutagenic, toxic or beneficial agents.

The lines according to the invention are also adapted to the expression of recombinant proteins. The methods of transfection of foreign DNA are now well known to persons skilled in the art (see for example PCT International Publication WO 94/05472).

The lines according to the invention also have a potential usefulness in gene therapy ex vivo. These lines might indeed constitute a suitable tool for developing recombinant cells expressing genes of interest for the purpose of a therapeutic application. One advantage additionally presented by the lines according to the invention is that they are not exposed to an animal serum, which considerably reduces the risks of potential contaminations by viruses or other pathogenic agents.

The present invention is described in greater detail below with the aid of the additional description which follows, which refers to examples of preparations of cell lines according to the invention. It goes without saying, however, that these examples are given by way of illustration of the subject of the invention and do not in any way constitute a limitation thereto. The culture of the cell lines, the preparation of SV40 vectors, the transfection, the preparation of DNA primers and probes and the analysis of the expressions of the markers are, unless otherwise stated, carried out according to the procedures described in the abovementioned references and in those in the manual by Sambrook et al. (Molecular Cloning, A Laboratory Manual, Cold Spring Harbor Laboratory Press, U.S.A., 1989). The percentages are given by weight, unless otherwise indicated.

EXAMPLE 1

The plasmid pl/SV40U19 is constructed by creating BamEII sites at the ends of the SV40 BglI-HpaI fragment and by cloning this fragment into the BamHI site of the plasmid pZIPSVtY19 described by Jat et al., Mol. Cell. Biol., 9, 1672–1681, 1989. As a guide, the vector pZIPSVU19 schematically represented in FIG. 1 comprises the selectable marker neomycin and the Moloney virus LTR.

The SV40 viruses are prepared according to a modified version of the Lynch and Miller procedure (J. Virol., 65, 3887–3890, 1991). For that, the ecotropic cell lines Psi2 (Mann et al., Cell, 33, 153–159, 1983) and the amphotropic cell lines PA317 (ATCC CR19078) are cultured in the DMEM medium (Dulbecco, USA) comprising 10% foetal calf serum, at 37° C. and under an atmosphere comprising 5% $CO_2$. These lines are conventionally transfected separately using 250 mM $CaCl_2$ and 10 μg of the plasmid pl/SV40U19, they are subjected to a treatment with trypsin after 48 h of incubation, they are mixed in an equal quantity, and the whole is incubated at 37° C. under an atmosphere comprising 5% $CO_2$. After growing to 80% confluence, the viruses are harvested in the serum-free medium KGM-1 (=KBM medium from Clonetics, US, comprising in addition 0.15 mM $CaCl_2$, 30 μg/ml of bovine pituitary gland extract, 0.5 μg/ml of hydrocortisone, 5 μg/ml of insulin, 10 μg/ml of transferrin, 10 ng/ml of murine epidermal growth factor (EGF), 10,000 U/ml of penicillin and 10,000 U/ml) of streptomycin). After filtration (0.45 μm, Micropore), the quantity of virus is determined on NIH 3T3 cells (ATCC CR1 1658).

Primary corneal epithelial cells were obtained following an eye biopsy on a 73-year old donor who died of myocardial infarction. The sample is washed in the phosphate buffer (PBS), it is treated at 4° C. for 24 h with 10 U/ml of dispase II (Boehringer Mannheim, No. 295825) in a buffer comprising 50% of KGM-2 medium (=KEM +0.05 mM $CaCl_2$, 30 μg/ml of bovine pituitary gland extract, 10 ng/ml of murine epidermal growth factor, 0.5 μg/ml of hydrocortisone, 0.05 μg/ml of amphotericin B, 5 μg/ml of insulin, 10 μg/ml of transferrin, 50 μg/ml of gentamycin). After incubation, the cells are separated manually, they are washed in DMEM medium (Dulbecco's modified Eagle medium, US) comprising 10% bovine foetal serum, they are centrfuged, the pellets are taken up in the KGM-2 medium and they are spread on culture plates previously preincubated in a 0.1% solution of gelatin A (Sigma G2500). The plates are incubated at 37° C. under an atmosphere comprising 100% relative humidity, 95% oxygen and 5% carbon dioxide. The culture medium containing the epithelial cells is changed as many times as is necessary to optimize a confluent growth.

After having reached a confluence of the order of 90% after 2 weeks of culture, the cells are conventionally separated by treatments in a solution of dispase II. The cells separated are then transferred into the KGM-1 medium and in culture plates preincubated with a 0.1% solution of gelatin A. The cultures are then infected in the presence of 8 μg/ml of polybrene and a high recombinant SV40 virus titre ($10^5$–$10^7$ CFU) prepared as described above. After 2 h of incubation with the virus, the cultures are washed in PBS and the cells are cultured by successive passages in fresh KGM-1 medium, taking care at each passage to successively wash the cells in an HBSS buffer (Hanks Balanced Salt Solution, Biofluids No. 325), to separate them by a treatment for 1–2 h at 37 W in a solution comprising 2.4 U/ml of dispase II, 50% HBSS buffer and 50% KBM medium, to harvest them in KEM medium, to centrifuge them and to take up the pellet in the KBM-1 medium and then to spread the cells on fresh new plates.

By successive passages, the transformed cells were purified from the primary epithelial cells. By then diluting, in a culture medium, the transformed cells previously separated by dispase II, it was possible to select 9 individualized immortalized human corneal epithelial cell lines of which one was deposited under the Budapest Treaty with the Collection Nationale de Cultures de Microorganismes, Institut Pasteur, 25 rue du Docteur Roux, 75724 Paris, on Oct. 22, 1996, where it received the deposit number CNCM I-1777.

1. Analysis of the Karyotype of the Strain CNCM I-1777

The analysis of the karyotype of the strain CNCM I-1777 was made by the "Children's Hospital of Michigan", 3901 Beaubien Blvd. Detroit, in accordance with the method described in the manual "Human cytogenetic", Edts: Rooney DE, Czepulkowski BH, IRL Press, Oxford, 1986. The results show that the line conserves intact in its genome one chromosome of each pair of chromosomes. The sex of the line is XX.

2. Tumoricienicity of the Strain CNCM I-1777

$10^7$ cells of the CNCM I-1777 line, taken at the 33rd passage, are injected into mice without immune defence ("nude") according to the procedure described by Stauffer et al. (The American Journal of Surgery, 169, 190–196, 1995). No tumour formation is visible after several months.

4. Viral Contamination of the CNCM I-1777 Line

It is determined whether the CNCM I-1777 line is contaminated by the hepatitis C virus (HCV), the hepatitis B virus (HBV) and the AIDS virus (HIV-1). The results of the experiments described below are negative for the presence of the 3 viruses.

For the analysis of HBV, DNA is extracted from about $2 \times 10^6$ cells by treating in phenol and chloroform solutions followed by a precipitation in ethanol. DNA samples are then subjected to a PCR amplification using primers specific for the pre-core region of the virus (Lynch et al.), J. Virol., 65, 3887–3890). The amplification products are then separated on an agarose gel and they are visualized under ultraviolet light (UV) in the presence of ethidium bromide. For comparison, a dilution of a serum containing 10–$10^5$ HBV (Anawa Biomedical Services 6 Product, USA) is analysed in the same manner, in parallel.

For the analysis of HIV-1, DNA samples described above are subjected to a PCR amplification using primers specific for the GAG region of the virus. The amplification products are then separated on an agarose gel and they are visualized under UV in the presence of ethidium bromide. For comparison, a dilution of a serum containing 10–$10^5$ HIV-1 (Anawa Biomedical Services 6 Product, USA) is analysed in the same manner, in parallel.

For the analysis of HCV, the RNA is extracted from about $2 \times 10^6$ cells by the method of Chomczynski et al. (Anal. Biochem., 162, 156–159, 1987). A reverse transcription is carried out conventionally, and the complementary DNA obtained is subjected to a PCR amplification using primers specific for the non-coding 5' region of the virus. The amplification products are then separated on an agarose gel and they are visualized under UV in the presence of ethidium bromide. For comparison, a dilution of a serum containing $10-10^5$ HCV (Anawa Biomedical Services Product, USA) is analysed in the same manner, in parallel.

5. Markers Specific for Human Epithelial Cells for the CNCM 1-1777 Line 5.a. Cytokeratins:

The cells of a culture of the CNCM I-1777 line, taken at the 22nd passage, are attached onto glass plates by a 100% cold methanol solution and then the plates are washed in a buffer comprising 0.05 M Tris pH 8.6, 1.8% NaCl and 0.2% polyethylene glycol 2000 (TNP buffer). The cells are then incubated for 30 mm in the presence of mouse antibodies specific for certain cytokeratins (anti-CH peptide 4, 7, 8, 13, 14, 17, 18, 19, 20; Sigma and Boehringer). After 3 washes in the TNP buffer comprising 0.5% bovine serum albumin (BSA), the plates are incubated for 60 mm with a goat anti-mouse IgG antibody comprising an immunofluorescent compound (1:300, FITC goat anti-mouse IgG; Biosys). After 3 washes in the preceding buffer, the plates are fixed and they are analysed by fluorescence microscopy. All the cells are positive for the cytokeratins 4, 7, 8, 13, 14, 17, 18, 19.

5.b. Vimentin:

The cells of a culture of the CNCM I-1777 line, taken at the 22nd passage, are attached as described above. The fixed cells are then subjected to a mouse anti-vimentin antibody (DAKO, USA), and then to the goat anti-mouse IgG antibody mentioned above. By fluor scence microscopy all the cells are positive for vimentin.

5.c. Connections Between the Cells:

The cells of the CNCM I-1777 line, taken at the 22nd passage, are cultured on a glass plate until they become confluent, they are fixed by treatment with a 2.5% glutaraldehyde solution in a 0.1 M phosphate buffer pH 7.4 for 1 h, at room temperature. After two washes in the same phosphate buffer, the cells are again fixed in a 2% $OsO_4$ solution in the same buffer. The cells are then dehydrated in successive solutions of ethanol at 30, 50, 70, 90 and 100% (Polaron Equipment Ltd., Watford, UK), and then the cells are covered by a fine gold layer (SEM coating unit E5100, Polaron). The cells are then examined by electron microscopy (Philips 505 SEM). The analysis shows that the cells have intercellular connections which are characteristic of the epithelial cells ("tight junctions").

5.d. Cytochrome P450:

The expression of cytochromes by the cells of the CNCM I-1777 line, taken at the 30th passage, is analysed with the aid of the known RT-PCR technique using DNA primers specific for the different cytochrome P450s. These primers were conventionally prepared from the DNA sequences of the different cytochromes available on the GenBank database (CYP1A1: accession No. X02612; CYP2C: accession No. M61855 or M61858 or M61856 or 14M61854; CYP2D6: accession No. M33388; CYP1A2: accession No. Z00036).

For that, the cells are cultured until they become confluent on 35 mm dishes (Costar), the RNA is extracted with the aid of the RNAeasy kit (Qiagen), a reverse transcription is performed (1st Strand cDNA Synthesis Kit for RT-PCR, Boehringer, Mannheim), the complementary DNA obtained is subjected to a PCR amplification using DNA primers specific for the different cytochrome P4SOs, the amplification products are then separated on an agarose gel, and they are visualized under UV in the presence of ethidium bromide. The results show that the CNCM I-1777 cells express cytochromes CYP1A1, CYP1A2, CYP2C, CYP2D6.

5.e. Enzymes Involved in the Cellular Oxidation and the Detoxification of Electrophiles:

The cells of the CNCM I-1777 line taken at the 30th passage are cultured, the RNA is extracted by the Chomczynski et al. method (Anal. Biochem., 162, 156–159, 1987), then a Northern-blot is performed on this ENA with DNA probes partially encoding Cu/Zn-superoxide dismutase (SOD), glutathione peroxidase (GP), catalase (CA) and π-glutathione-S-transferase (πGST). The DNA probes are prepared conventionally from DNA sequences of the genes encoding these enzymes which are available on the GenBank database (πGST: accession No. X08058; GP: accession No. M21304; CA: accession No. M81578; SOD: accession No. 729336). The results of these tests show that all the cells express a transcription of the genes encoding the SOD, GP, CA and πGST activity.

Moreover, the expression of glutathione reductase is also confirmed by the enzymatic test described by Gondhowiardjo (Cornea, 12, 3 10–314, 1993). The catalase activity is also confirmed by the enzymatic test described by Aeby et al. (Method and Enzymology, 105, 121–126, 1984). Finally, the aldehyde reductase activity is also demonstrated by the enzymatic test described by Ellis et al. (Biochemical Journal, 312, 535–541, 1995).

6. Markers Specific for the Epithelial Cells of the Cornea for the CNCM I-1777 Line 6.a. Expression of the Cytokeratin of 64 kfl:

As for the analysis of the cytokeratins described above, the cells are attached onto glass plates by a 100% cold methanol solution and then the plates are washed in TNP buffer (see above). The cells are then incubated for 30 mm in the presence of mouse antibodies specific for the 64 kD cytokeratin (AES antibody, 1CM Biomedical Inc., US). After 3 washes in the TNP buffer comprising 0.5% BSA, the plates are incubated for 30 mm with a goat anti-mouse IgG antibody comprising an immunofluorescent compound (1:300, FITC-goat anti-mouse IgG; Biosys). After 3 washes in the preceding buffer, the plates are fixed and they are analysed by fluorescence microscopy. The cells are positive for the 64 kD cytokeratin.

6.b. Expression of Glutathione-S-transferase hGST 5.8:

The expression of glutathione-S-transferase hGST 5.8 is analysed by means of the test described by Singhal et al. (Invest. Ophthalmol. Vis. Sci., 36, 142–150, 1995). In short, 10 μg/ml of a cytosolic extract of the CNCM I-1777 line is mixed with 0.1 mM 4-hydroxynonenal and 0.5 mM glutathione in a 100 mM potassium phosphate buffer pH 6.5 and then the enzymatic activity is measured by the change in absorption in the mixture at 224 nm. The results show that the CNCM I-1777 line expresses a glutathione-S-transferase hGST 5.8 activity.

6.c. Profile of Expression of the Cytokines and Growth Factors:

The cells of the CNCM I-1777 line taken at the 30th passage are cultured, the RNA is extracted and then a PCR is performed on this ENA with different primers in order to confirm the transcription of the R.NAs encoding the cytokines and/or growth factors which follow: TNFα, IL-1β, IL-1α, IL-6, IL-8, GM CSF-β, IL-ra, TGF-β1, TGFβ2, TGFα, EGF and PDGF-β.

These primers correspond to a portion of the genes encoding these compounds, the DNA sequences of the said genes being accessible on the GenBank database (TNFα: Accession No. X02910; IL-β: Accession No. M15840;

IL-1α: Accession No. M15329; IL-6: Accession No. M14584, Rosenbaum et al., Invest. Opthalmol. Vis. Sci., 36, 2151–2155, 1995; IL8: Accession No. M28130; GM CSF-β: Accession No. X03021; IL-ra: Accession No. M97748, Kennedy et al., J. Clinical Inv., 95, 82–88, 1995; TGF-β1: Accession No. X02812, Nishida et al., Curr. Eye Res., 14, 235–241, 1995; TGF-β2: Accession No. Y00083; TGFa: Accession No. M22440; EGF: Accession No. L17032; PDGF-β: Accession No. X02811).

For comparison, the same analysis of the profile of expression of the cytokines and growth factors is performed on the RNA derived from epithelial tissues of the human cornea (4 different biopsies).

The results are presented in Table 1 below. The symbol * indicates that the expression of the compounds IL-β, TNFα, IL-1α, IL-6 and IL-8 was also confirmed by ELISA tests using the CNCM I-1777 cell culture medium.

The specific antibodies against these different cytokines are commercially available (IL-β, TNFα: BioSource Inter., US, catalogue No. KHC0012 and KHC3013; IL-1α, IL-6 and IL-8: CLB corp., US, catalogue No. M1901, M1916, M1918).

TABLE 1

| Cytokines & growth factors | CNCM I-1777 | Biopsy 1 | Biopsy 2 | Biopsy 3 | Biopsy 4 |
| --- | --- | --- | --- | --- | --- |
| TNFα* | + | +/− | +/− | +/− | +/− |
| IL-1β* | +++ | + | ++ | + | ++ |
| IL-1α* | +++ | +/− | ++ | + | +++ |
| IL-6* | ++ | + | + | − | − |
| IL-8* | +++ | +/− | + | + | ++ |
| GM CSF-β | ++ | +/− | +/− | +/− | +/− |
| IL-ra | ++ | + | +++ | ++ | + |
| TGF-β1 | +++ | + | ++ | + | ++ |
| TGF-β2 | +++ | + | ++ | ++ | ++ |
| TGFα | +++ | + | ++ | + | ++ |
| EGF | +++ | + | + | ++ | +++ |
| PDGF-β | + | +/− | +/− | +/− | +/− |

(−: not detected; +/−: weakly detected; +++: abundant)

7. Markers Specific for an Inflammatory Reaction for the CNCM I-1777 Line 7.a. Collagenase I:

Collagenase I is a molecule whose expression characterizes a normal state of inflammation of the cornea). cells. The expression of collagenase can be detected by PCR, by Western-blotting or by enzyme linked immunsorbant assay (ELISA).

To detect collagenase I by PCR, the CNCM I-1777 cells, taken at the 29th passage, are cultured in the presence of 20 ng/ml of TPA for 16 to 24 h, the RNA is extracted and the presence of collagenase I mRNA is detected by PCR with a primer derived from the collagenase I DNA sequence (GenBank: No. X05231).

To detect collagenase I by Western blotting, after having cultured the CNCM I-1777 cells in the prpsence of 20 ng/ml of TPA for 16 to 24 h, the culture medium is recovered and it is concentrated with an AMICON30® filter, the protein is separated by electro-phoresis on an SDS polyacrylamide-gel electrophoresis (SDS-Page) polyacrylamide gel, they are transferred by Western blotting onto a filter, the filter is subjected to a first anti-collagenase I antibody (Cortex Biochem, US, No. 60338P), to a second antibody coupled to a peroxidase (Pierce, US, No. 31400), and then to the peroxidase substrate.

To detect collagenase I by ELISA, it is sufficient to use the Amersham bMMP-1 kit (catalogue, rpn 2610), following the recommendations of the supplier.

The results show that the expression of collagenase I can be detected when the CNCM I-1777 cells are subjected to an inflammatory treatment. On the other hand, when the CNCM I-1777 cells are not brought into contact with TPA, they do not express collagenase I which is detectable by PCR, Western blotting or ELISA.

7.b. Markers Necessary for an Inflammatory Reaction:

The bradykinin, histamine and PAP receptors and the system for transduction of the phosphoinositides are markers essentially for the CNCM I-1777 line to be physiologically in a normal state of inflammation. To detect the presence of these markers, the CNCM I-1777 cells or primary epithelial cells of the human cornea are incubated in the presence of inflammatory compounds which are supposed to interact with receptors coupled with the system for transduction of inflammatory signals by the phosphoinositides, and the concentration of inositol phosphate (IP) molecules thus produced is measured. The accumulation of IP is in fact characteristic of the existence of receptors for the inflammatory compounds.

The tests are based on the procedures by Sharifs et a). described in J. Ocular Pharmacol., 10, 653–664, 1994; and Neurochem Res., 12, 1313–1320, 1993. In short, on plates comprising 24 wells, about $2.5 \times 10^5$ CNCM I-1777 cells per well are cultured in DMEM medium in the presence of [$^3$H]myo-inositol (1 μCi/0.5 ml; 15–17 Ci/mM, Amersham Corp.), for 24 h at 37 W. The medium is sucked up from the wells and they are exposed for 60 mm at 37 W to DMEM medium comprising 10 mM LiC), 15 mM HEPES buffer, and different concentrations of bradykinin (Collaborative Biomedical, US), of histamine (Sigma, US) or of PAP (BioMol Research Lab, US). To stop the reaction, the medium is then sucked up and 0.1 M formic acid is added to the wells. After that, the cells are lysed and the compounds of the lysate are separated on an ion-exchange column (AGlx8 resin, ECONO® column, Biorad, US), eluting the column with 10 ml of deionized water and 8 ml of a 50 mM ammonium formate solution, and the radioactivity released by the elution fractions is quantified with a scintillation counter.

The results are analysed according to the method described by Sharif et al. (Neurochem. Int., 18, 89–96, 1991). The ECSO value defines the concentration of compound required to stimulate 50% of the maximum activity of the system for transduction of the phosphoinositides.

Figure 2:
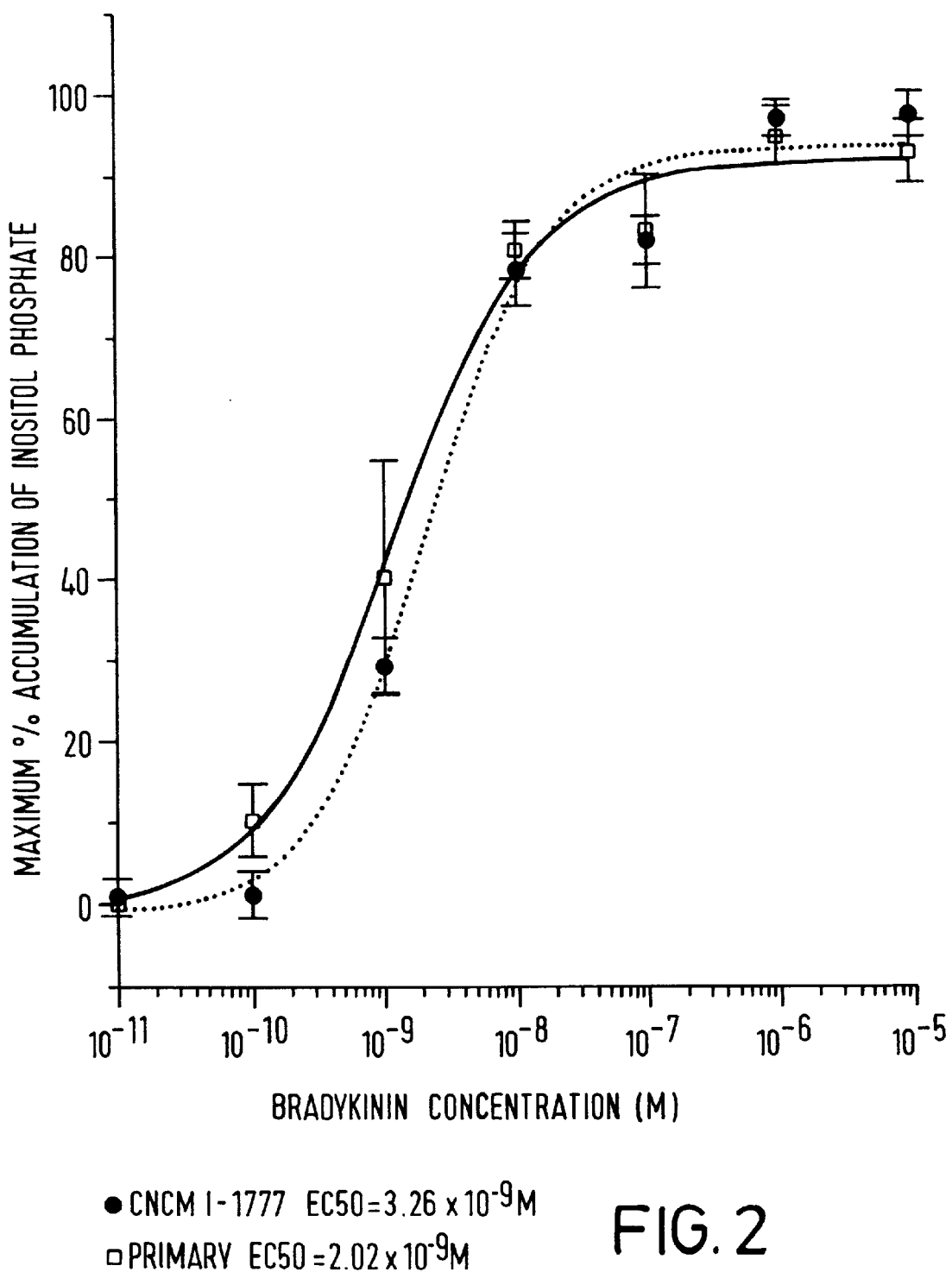
FIG. 2: percentage accumulation of [$^3$H] phosphoinositides by primary epithelial cells of the human cornea and by the CNCM I-1777 cells, as a function of the applied bradykinin concentration.
Figure 3:
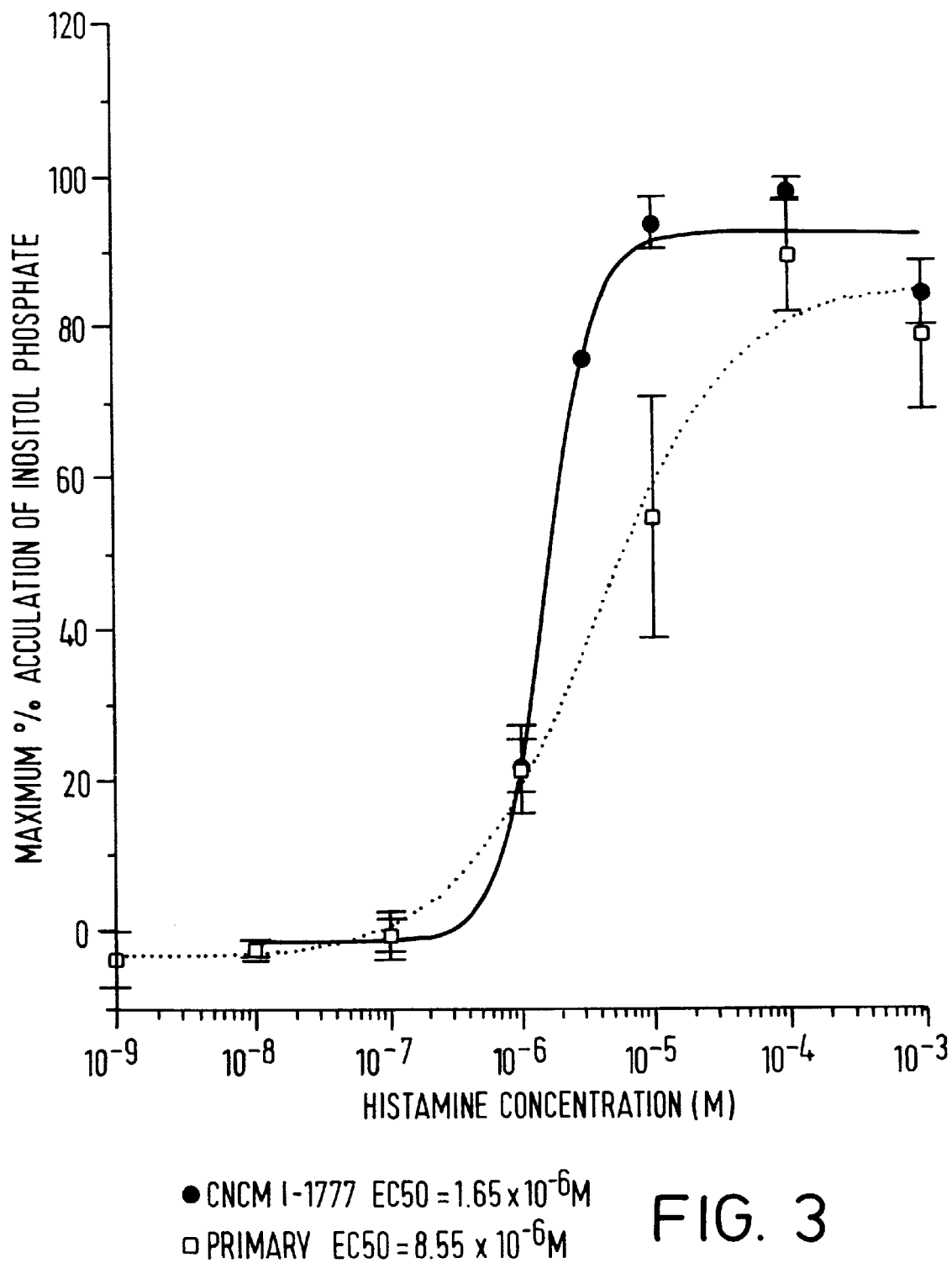
FIG. 3: percentage accumulation of [$^3$H] phosphoinositides by primary epithelial cells of the human cornea and by the CNCM I-1777 cells, as a function of the applied histamine concentration.
Figure 4:
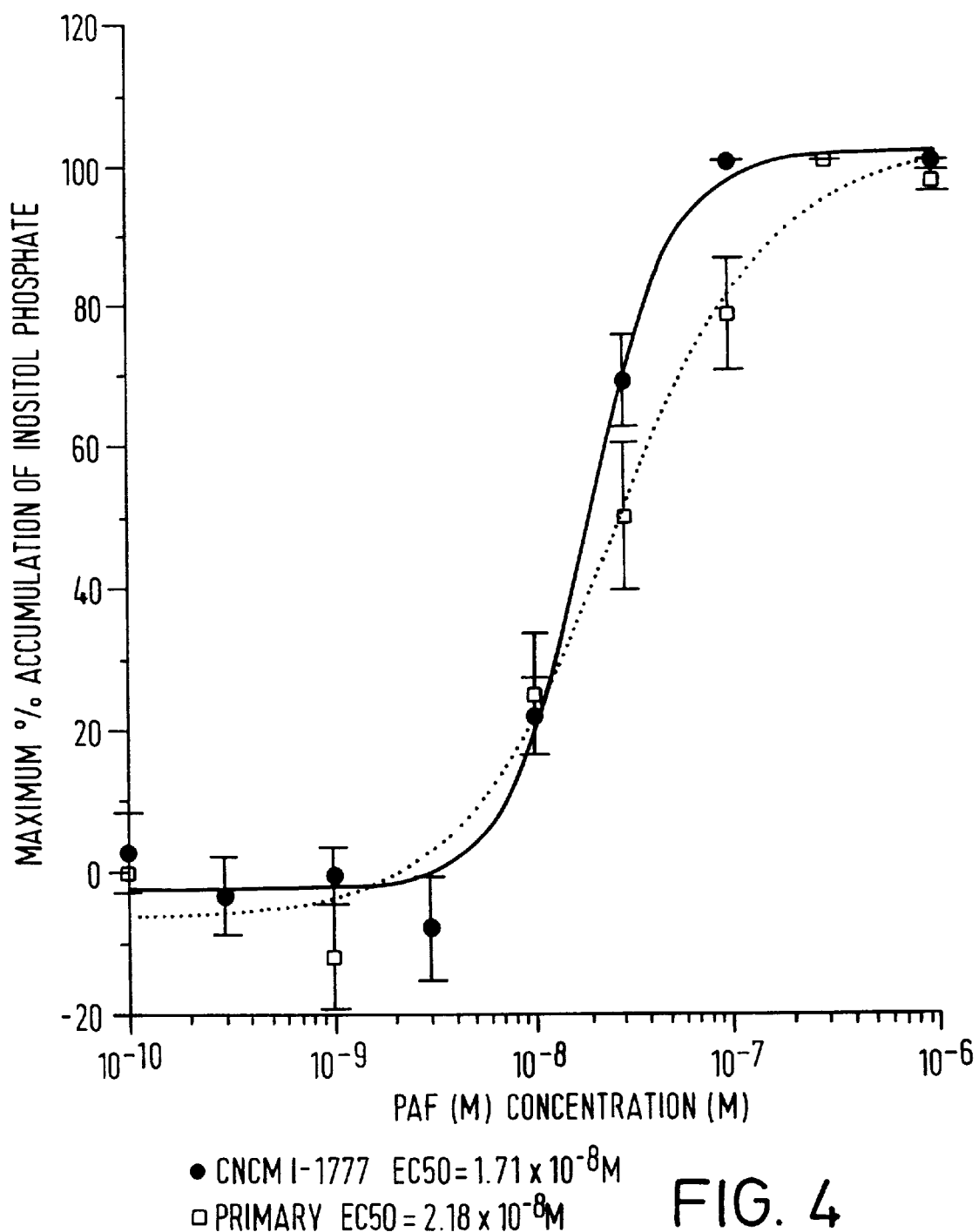
FIG. 4: percentage accumulation of [$^3$H] phosphoinositides by primary epithelial cells of the human cornea and by the CNCM I-1777 cells, as a function of the applied platelet activating factor (PAF) concentration.

The results, presented in FIGS. 2, 3 and 4, show that the CNCM I-1777 cells have bradykinin, histamine and PAP receptors and that they behave like primary epithelial cells of human cornea.

EXAMPLE 2

As described in Example 1, the capacity of the CNCM I-1777 line taken at the 106 passage to express metabolic markers specific for non-immortalized human epithelial cells, metabolic differentiation markers specific for the non-immortalized epithelial cells of the human cornea, and markers for an inflammatory reaction, is analysed. The results are comparable to those presented in Example 1.

EXAMPLE 3

As described in Example 1, the capacity of the other lines selected in Example 1 to express metabolic markers specific for the non-immortalized human epithelial cells, metabolic differentiation markers specific for the non-immortalized epithelial cells of the human cornea, and markers for an inflammatory reaction, is analysed. For all these lines, the results are comparable to those presented in Example 1.

What is claimed is:

1. An immortalized cell line which has the deposit number CNCM I-1777.

2. A method for determining mutagenic, toxic or beneficial effects of an agent on metabolism of cornea cells, which comprises: reacting, culturing or contacting a culture comprising the cell line of claim 1 with the agent; and determining or measuring the mutagenic, toxic or beneficial effects of the agent on the cell line.

3. A diagnostic kit for identifying a mutagenic, toxic, or beneficial agent on the metabolism of cornea cells comprising: (a) a cell line which has the deposit number CNCM I-1777; and (b) reagents for determining a metabolic response of the cell line to mutagenic, toxic or beneficial agents.

4. The diagnostic kit of claim 3, wherein the reagents comprise a nucleic acid or an antibody.

5. The diagnostic kit of claim 3, wherein the reagents detect collagenase I.

* * * * *

UNITED STATES PATENT AND TRADEMARK OFFICE
CERTIFICATE OF CORRECTION

PATENT NO. : 6,284,537 B1  
DATED : September 4, 2001  
INVENTOR(S) : Offord Cavin et al.

Page 1 of 1

It is certified that error appears in the above-identified patent and that said Letters Patent is hereby corrected as shown below:

Title page,
Column 1,
Under the heading, "OTHER PUBLICATIONS",
Lines 8 and 10, change "*Invest*" to -- *Invest.* --
Line 15, change "-free" to -- free --
Line 21, change "gasstrointestinal" to -- gastrointestinal --
Line 22, change "*Visu*" to -- *Visu.* --
Line 30, change "-immortalized" to -- immortalized --

Column 2,
Line 2, change "*Invest*" to -- *Invest.* --
Line 4, change "et al. 1995," to -- et al., 1995, --
Line 8, change "Sherif" to -- Sharif --
Line 9, change "phophoinositide" to -- phosphoinositide --
Line 18, change "*Tiss*" to -- *Tiss.* --
Line 31, change "*Ana*" to -- *Ana.* --

ABSTRACT,
Line 10, change "sstransferase" to -- S-transferase --.

Signed and Sealed this

Twenty-sixth Day of February, 2002

*Attest:*

*Attesting Officer*

JAMES E. ROGAN
*Director of the United States Patent and Trademark Office*

UNITED STATES PATENT AND TRADEMARK OFFICE
CERTIFICATE OF CORRECTION

PATENT NO.     : 6,284,537 B1
DATED          : September 4, 2001
INVENTOR(S)    : Offord Cavin et al.

It is certified that error appears in the above-identified patent and that said Letters Patent is hereby corrected as shown below:

Title page,
Under the heading, "OTHER PUBLICATIONS",
Araki et al., reference change "*Invest*" to -- *Invest.* --
Araki-Sasaki et al. reference change "*Invest*" to -- *Invest.* --
Conners et al., reference change "*Visu*" to -- *Visu.* --
Cubitt et al., reference change "*Invest*" to -- *Invest.* --
2nd Cubitt et al. reference change "et al. 1995," to -- et al., 1995, --
Hainsworth, reference change "*Tiss*" to -- *Tiss.* --
Lynch et al., reference change "-free" to -- free --
McKinmon et al., reference change "gasstrointestinal" to -- gastrointestinal --
Pfiefer et al., reference change "-immortalized" to -- immortalized --
Sherif et al., reference change "Sherif" to -- Sharif --; and change "phophoinositide" to -- phosphoinositide --
Wilson et al., reference, change "*Ana*" to -- *Ana.* --

ABSTRACT,
Line 10, change "sstransferase" to -- S-transferase --.

This certificate supersedes Certificate of Correction issued February 26, 2002

Signed and Sealed this

Sixteenth Day of July, 2002

*Attest:*

JAMES E. ROGAN
*Attesting Officer*     *Director of the United States Patent and Trademark Office*